US011231310B2

(12) United States Patent  
Strong

(10) Patent No.: US 11,231,310 B2  
(45) Date of Patent: Jan. 25, 2022

(54) FLUID LEVEL AND COMPOSITION SENSOR

(71) Applicant: Tigmill Technologies, LLC, Farmers Branch, TX (US)

(72) Inventor: Bobby David Strong, Sachse, TX (US)

(73) Assignee: Tigmill Technologies, LLC, Farmers Branch, TX (US)

( * ) Notice: Subject to any disclaimer, the term of this patent is extended or adjusted under 35 U.S.C. 154(b) by 775 days.

(21) Appl. No.: 15/821,520

(22) Filed: Nov. 22, 2017

(65) Prior Publication Data

US 2018/0143061 A1 May 24, 2018

Related U.S. Application Data

(60) Provisional application No. 62/425,960, filed on Nov. 23, 2016.

(51) Int. Cl.

| | |
|---|---|
| *G01F 23/284* | (2006.01) |
| *G01N 23/10* | (2018.01) |
| *G01N 23/06* | (2018.01) |
| *G01F 23/26* | (2006.01) |
| *G01N 33/28* | (2006.01) |
| *G01F 23/04* | (2006.01) |
| *G01F 23/24* | (2006.01) |

(52) U.S. Cl.  
CPC ............ *G01F 23/284* (2013.01); *G01F 23/04* (2013.01); *G01F 23/245* (2013.01); *G01F 23/263* (2013.01); *G01N 23/06* (2013.01); *G01N 23/10* (2013.01); *G01N 33/2847* (2013.01)

(58) Field of Classification Search  
CPC ...... G01F 23/284; G01F 23/04; G01F 23/245; G01F 23/263; G01N 33/2847; G01N 23/10; G01N 23/06  
See application file for complete search history.

(56) References Cited

U.S. PATENT DOCUMENTS

| | | | | |
|---|---|---|---|---|
| 3,533,286 A | * | 10/1970 | Blanchard | ............. G01F 23/266 |
| | | | | 73/304 C |
| 3,965,983 A | | 6/1976 | Watson | |
| 3,980,881 A | | 9/1976 | Veach et al. | |
| 4,321,826 A | * | 3/1982 | Bibbee | ................... G01F 1/005 |
| | | | | 73/215 |
| 5,035,581 A | | 7/1991 | McGuire et al. | |
| 5,103,181 A | * | 4/1992 | Gaisford | ............ G01N 33/2823 |
| | | | | 324/637 |
| 5,597,042 A | | 1/1997 | Tubel et al. | |

(Continued)

*Primary Examiner* — Marrit Eyassu  
(74) *Attorney, Agent, or Firm* — Slater Matsil, LLP

(57) ABSTRACT

A fluid sensor system comprises a radio frequency transmitter with adjustable output power, a radio frequency detector proximal to the radio frequency transmitter; a constant current source, and a switch coupled between the radio frequency detector and the constant current source. A method of determining the identity of a fluid using the fluid sensor system includes immersing the sensor system in a first fluid, increasing a transmit power of a radio frequency (RF) transmitter of the fluid sensor system until an RF signal is detected by a RF detector of the fluid sensor system, and determining the transmit power of the RF transmitter that first resulted in a detection of the RF signal by the RF detector to be the transmit power that is required for detecting the RF signal in the first fluid.

7 Claims, 8 Drawing Sheets

(56) References Cited

U.S. PATENT DOCUMENTS

| | | | |
|---|---|---|---|
| 5,662,165 A | 9/1997 | Tubel et al. | |
| 6,497,281 B2 | 12/2002 | Vann | |
| 6,556,014 B1* | 4/2003 | Kong | G01V 3/30 324/338 |
| 8,235,111 B2 | 8/2012 | Fink | |
| 9,488,531 B2 | 11/2016 | Wysocki et al. | |
| 2007/0040557 A1* | 2/2007 | Johnstad | G01F 23/284 324/324 |
| 2010/0073189 A1 | 3/2010 | Mandal et al. | |
| 2010/0114534 A1 | 5/2010 | Gratzer et al. | |
| 2012/0151994 A1* | 6/2012 | Hung | G01N 21/1702 73/24.02 |
| 2013/0068008 A1 | 3/2013 | Kahler et al. | |
| 2014/0367092 A1* | 12/2014 | Roberson | E21B 47/01 166/250.01 |
| 2015/0063418 A1 | 3/2015 | Wysocki et al. | |
| 2015/0292956 A1 | 10/2015 | Mitchell et al. | |
| 2015/0300891 A1 | 10/2015 | Mitchell et al. | |
| 2016/0024915 A1 | 1/2016 | Duchene et al. | |
| 2016/0024916 A1 | 1/2016 | de Oliveira et al. | |
| 2017/0038311 A1* | 2/2017 | Conrad | G01N 33/2888 |
| 2018/0059280 A1* | 3/2018 | Hartmann | G01V 3/30 |

\* cited by examiner

FLUID LEVEL AND COMPOSITION SENSOR

REFERENCE TO RELATED APPLICATIONS

This application claims priority to U.S. Provisional Application No. 62/425,960, filed Nov. 23, 2016, which is incorporated herein by reference in its entirety.

TECHNICAL FIELD

This invention relates to the field of sensors. More particularly, this invention relations to fluid composition and/or fluid level sensors.

BACKGROUND

The presence of a liquid or fluid or the level of a liquid or fluid in a vessel is sometimes measured using a sensor with moving parts, such as a float. Some liquids may contain debris that may foul these sensors, causing them to fail.

Some sensors may be coupled to a controller that reads signals from the sensor. In some applications a sensor may be located a long distance from the controller that reads the sensor signal. For example, in some industrial applications the controller may be at a well head whereas the sensor may be many thousands of feet down a well hole. Certain sensors produce a voltage signal to indicate the presence or absence of the liquid. The voltage signal at the controller may be degraded when a cable connecting the sensor to the controller becomes more resistive due to, for example, age or increased length. As such, in situations where a sensor is located a relatively large distance from a controller to which it is coupled may experience signal degradation, which may decrease reliability of the signal.

In some applications it is of interest to know the composition of a fluid or liquid mixture. For example, in some situations it may be of interest to know the percentage of oil versus the percentage of water is in a liquid mixture. Since oil has a dielectric constant of about 2 and water has a dielectric constant of about 78, the dielectric constant of a mixture of oil and water may increase as the fraction of water in the mixture increases.

DETAILED DESCRIPTION

Figure 1:
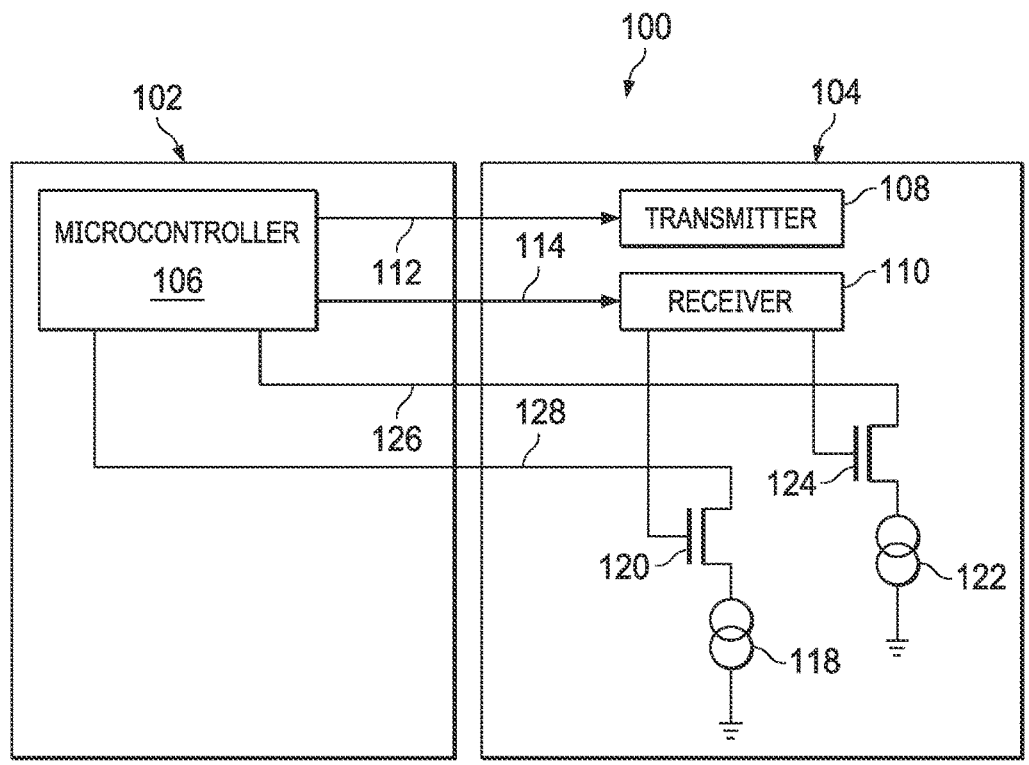
FIG. 1 depicts a sensor system in accordance with some embodiments.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It is understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

A RF dielectric sensor detection system (sensor system) 100 is depicted in FIG. 1. The sensor system 100 may include a controller unit 102 and a sensor unit 104. Sensor unit 104 is configured to be submerged in a fluid such as air, natural gas, oil, or water. The sensor system 100 may detect the presence of certain fluids based upon the dielectric constant of the fluid in which the sensor unit 104 is submerged. Sensor system 100 depicted in FIG. 1 may be configured to detect which of two different fluids such as air and water, air and oil, or oil and water is present. In some embodiments, more than two fluids may be detected.

The controller unit 102 may be connected to the sensor unit 104 by conductive paths 112, 114, 126 and 128. Sensor unit 104 may be disposed in a fluid. For example, sensor unit 104 may be disposed in a fluid such as air, oil, or water in a well. In some embodiments, controller unit 102 may be located remotely from sensor unit 104. For example, controller unit 102 may be located at or proximate to a well head.

The sensor unit 104 includes a transmitter 108 and a receiver 110. The receiver may also be referred to as a detector in some embodiments. The transmitter 108 may be configured to output a radio frequency (RF) signal, and receiver 110 may be configured to detect the RF signal. For example, receiver 110 may be tuned to detect the RF signal transmitted by transmitter 108 in some embodiments. The transmitter 108 may be configured to output RF signals having different transmit powers. The strength (for example, the transmit power) of the RF signal that is outputted by transmitter 108 may depend on a signal sent by the microcontroller 106 in the controller unit 102 to the transmitter 108 in the sensor unit 104 over conductive path 112.

During operation of the sensor circuit 100, an RF signal is transmitted from transmitter 108 into the medium in which the sensor unit 104 is disposed, and the receiver 110 attempts to receive the transmitted RF signal through the medium. For example, the sensor unit 104 may be disposed in a fluid, and the RF signal may be transmitted from transmitter 108 into the fluid, and the receiver may attempt to receive the transmitted RF signal through the fluid. The transmission of the RF signal may depend on a dielectric constant of the medium. For example, the transmission of the RF signal may be improved as the dielectric constant of the medium is increased, and the transmission of the RF signal may decline as the dielectric constant of the medium is decreased. In some embodiments, an RF signal having a given transmit power may be received by the receiver 110 when the sensor unit 104 is disposed in a fluid having a higher dielectric constant, and may not be received by the receiver 110 when the sensor unit 104 is disposed in a fluid having a lower dielectric constant. By determining whether the RF signal transmitted by the transmitter 108 at a certain transmit power is received by the receiver 110, the sensor system 100 may detect the presence (or lack of presence) of a fluid whose required transmit power level for successful detection is known.

Figure 2:
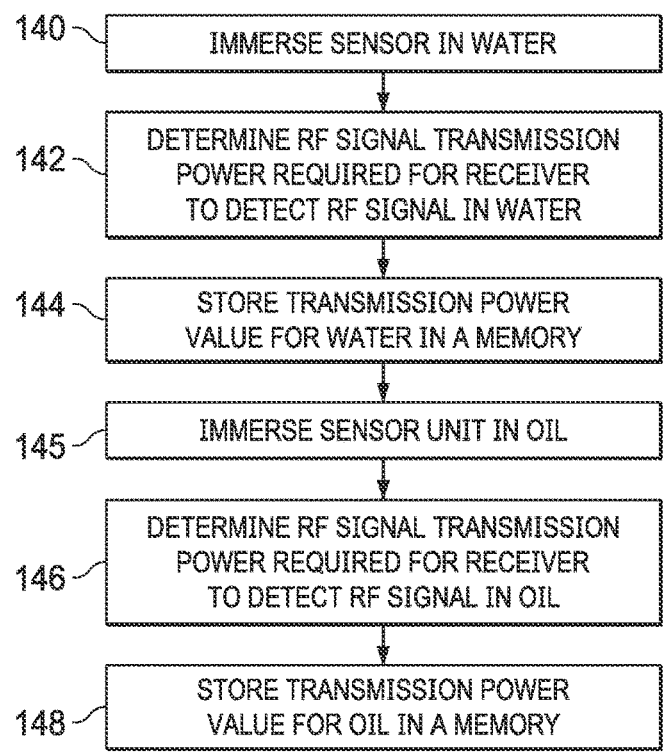
FIG. 2 depicts a method of calibrating a sensor system in accordance with some embodiments.

FIG. 2 depicts a method of calibrating a sensor unit, such as the sensor system 100 depicted in FIG. 1, according to some embodiments. Physical components referred to in the method of FIG. 2 are depicted in the sensor system 100 of FIG. 1. For illustration purposes only, the detection of air, oil, and/or water in an oil well is discussed. Other applications and detections of other fluids are contemplated.

In some embodiments, the sensor unit 104 may be calibrated before being positioned inside the well. A calibration method begins in step 140, in which the sensor unit 104 is immersed in water. Next, in step 142, the transmit power of the RF signal required to transmit the RF signal through water and be successfully received by the receiver 110 is determined. In some embodiments, the transmit power of the RF signal may initially be set to a low value, and then gradually increased until the receiver 110 first detects the RF signal. The transmit power of the RF signal that is used when the receiver 110 first detects the RF signal may be determined to be the transmit power that is required to detect the RF signal in water. In some other embodiments, the transmit power of the RF signal may initially be set to a high value, and then gradually decreased until the receiver 110 is no longer able to detect the RF signal. The last transmit power that resulted in a detected RF signal may be determined to be the transmit power that is required to detect the RF signal in water.

In some embodiments, detection of the RF signal by the receiver 110 may occur whenever receiver 110 is able to receive the RF signal. In other embodiments, the receiver 110 may be configured to detect the RF signal when a received transmit power of the RF signal is above a predetermined threshold. In step 144, the determined transmit power for transmitting the RF signal through water is stored in the memory of the microcontroller 106.

Next, in step 145, the sensor unit 104 is immersed in oil (e.g. crude oil as may be found in a well). In step 146 the required transmit power of the RF signal for transmitting the RF signal through oil is determined using the same or similar method as those described above for determining the transmit power for transmitting the RF signal through water. In step 148 the transmit power for transmitting the RF signal through oil is stored in the memory of microcontroller 106.

By determining the transmit power of the RF signal that is required for the receiver 110 to detect the RF signal transmitted by the transmitter 108 when the sensor unit 104 is respectively immersed in water and oil, a composition of the fluid in which the sensor unit 104 is disposed may be determined. For example, in some oil well applications the fluid in which the sensor unit 104 is disposed may comprise one or a combination of water, crude oil, and air. Water has a higher dielectric constant than crude oil, and crude oil has a higher dielectric constant than air. For example, water has a dielectric constant of about 78, crude oil has a dielectric constant of about 2.1, and air has a dielectric constant of about 1. As discussed above, given a same transmit power of the RF signal, the detection of the RF signal by the receiver 110 may be depend on whether the sensor unit 104 is immersed in oil, water, or air. For example, since crude oil has a higher dielectric constant (about 2.1) than air (about 1), a weaker (lower transmit power) RF signal may be detected by the receiver 110 when the sensor unit 104 is immersed in oil than when it is immersed in air. Similarly, a weaker RF signal may be detected by the receiver 110 when the sensor unit 104 is immersed in water than when it is immersed in oil or air.

Figure 3:
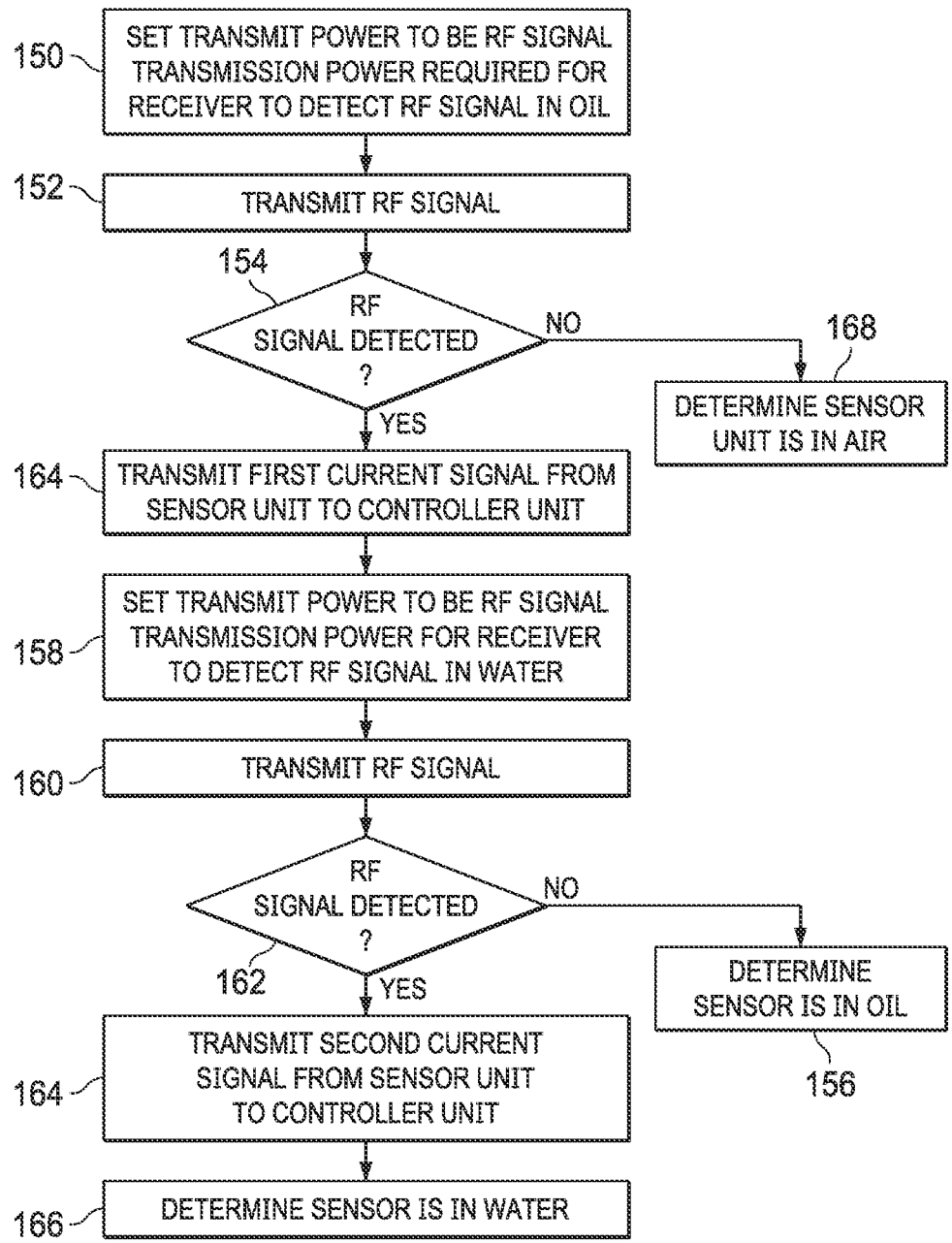
FIG. 3 depicts a method of operating a sensor system in accordance with some embodiments.

According to the discussion above, FIG. 3 depicts a method of using a sensor system (for example sensor system 100 depicted in FIG. 1) to determine the composition of a liquid or fluid in an oil well. Physical components referred to in the method of FIG. 3 are depicted in the sensor system 100 of FIG. 1. In step 150, the transmit power of the RF signal that is transmitted from transmitter 108 is adjusted to be the RF transmit power for detecting oil. In some embodiments, microcontroller 106 may send a signal to the transmitter 108 on conductive path 112 to adjust the transmit power of the RF signal transmitted by the transmitter 108 to correspond to the transmit power of the RF signal for oil detection. The transmit power of the RF signal for oil detection may have been predetermined and or stored in a memory of the microcontroller 106, for example as described in connection with FIG. 2. As such, the microcontroller 106 may retrieve the stored transmit power of the RF signal for oil detection, and send it to the transmitter 108 to instruct the transmitter 108 to transmit an RF signal using a transmit power that corresponds to the stored transmit power of the RF signal for oil detection. The microcontroller 106 also sends a signal on conductive path 114 to the receiver 110 indicating that the RF transmit power of the transmitter 108 is set at the RF transmit power for oil detection. In step 152, the transmitter 108 transmits the RF signal with the instructed transmit power for oil detection. In step 154, depending upon the fluid in which the sensor unit 102 is immersed, the receiver 110 either detects the RF signal, or does not detect the transmitted RF signal.

If the transmitted RF signal is not detected in step 154, in step 168 it is determined that the sensor unit 104 is in air. For example, the microcontroller 106 may determine that the sensor unit 104 is in air after not receiving a current signal from the sensor unit 104 for a predetermined period of time after instructing the transmitter 108 to transmit the RF signal using the transmit power for oil detection.

If the sensor unit 104 is in oil (or water, because water has a higher dielectric constant than oil), in step 154 the receiver 110 detects the RF signal. In some embodiments, receiver 110 may detect the signal by receiving the RF signal at any signal power. In other embodiments, receiver 110 may detect the signal by receiving the RF signal having a signal power that is greater than a predetermined threshold. In step 164, logic in the receiver 110 turns on transistor 120 which connects a current source 118 to the microcontroller 106 using conductive path 128, thereby sending a first current signal from the sensor unit 104 to the microcontroller 106 in the controller unit 102 indicating that the sensor unit 104 has detected the transmitted RF signal. The microcontroller 106 may store, for example in a memory, an association between the first current signal and oil. Because a current signal from current source 118 is used to indicate to the microcontroller 106 the detection of the transmitted RF signal, conductive path 128 may be relatively lengthy and the transmitted signal may still be reliably transmitted. For example, when a current signal is used instead of a voltage signal, the signal may be less sensitive to degradation due to, for example, increased resistivity of conductive path 128 due for example to age or normal wear and tear.

Next, it may be determined whether the sensor unit 104 is in water. In step 158, the transmit power of the RF signal is adjusted to be the RF transmit power for detecting water. The transmit power of the RF signal for water detection may have been predetermined and or stored in a memory of the microcontroller 106, for example as described in connection with FIG. 2. As such, the microcontroller 106 may retrieve the stored transmit power of the RF signal for water detection, and send it to the transmitter 108 to instruct the transmitter 108 to transmit an RF signal using a transmit power that corresponds to the stored transmit power of the RF signal for water detection. In some embodiments, the microcontroller 106 may send a current signal to the transmitter 108 on conductive path 112 to instruct the transmitter 108 to decrease the transmit power of the RF signal to be the RF transmit power for detecting water. The microcontroller 106 also sends a signal to the receiver 110 on conductive path 114 indicating that the RF transmit power of the transmitter 108 is set at the transmit power for detecting water. In step 160, the RF signal is transmitted by the transmitter 108 with the transmit power for detecting water. In step 162, the receiver 110 either detects the transmitted RF signal or does not detect the transmitted RF signal.

If the transmitted RF signal is not detected in step 162, in step 156 it is determined that the sensor unit 104 is in oil. For example, the microcontroller 106 may determine that the sensor unit 104 is in oil after not receiving a current signal from the sensor unit 104 for a predetermined period of time after instructing the transmitter 108 to transmit the RF signal at the transmit power for detecting water.

If the transmitted RF signal is detected, in step 164 logic in the receiver 110 turns on transistor 124 which connects a current source 122 to the microcontroller 106 using conductive path 126, thereby sending a second current signal to the microcontroller 106 indicating that the transmitted RF signal has been detected. In some embodiments, a current that is provided by current source 118 has a magnitude that is different than a current that is provided by current source 122. As such, microcontroller 106 is able to distinguish between the first current signal and the second current signal. For example, the microcontroller 106 may store, for example in a memory, an association between the first current signal and oil, and the second current signal and water.

In step 166, it is determined that the sensor unit 104 is in water. For example, the microcontroller 106 may determine that the sensor unit 104 is in water after receiving the second current signal from the sensor unit 104.

In some embodiments, the method of FIG. 3 may be used to determine fluid levels in an oil well. For example, the sensor unit 104 is lowered down into the well. In some embodiments, the sensor system 100 may be set to repeatedly perform sequential detections (for example, using the method of FIG. 3) to determine the medium in which the sensor unit 104 is immersed. For example, the sensor unit 104 may be set to repeatedly perform sequential detections and then lowered into a well. In some cases, fluids at the top of a well may include air. As such, the sensor unit 104, upon entering the well, may first send no signal to the controller unit 102, indicating that the sensor unit is in air. When the sensor unit 104 passes from air into oil as it is being lowered into the well, the sensor unit 104 may then send a current signal to microcontroller 106 to indicate it is now immersed in oil. The length of the conductive paths 112, 114, 126, and/or 128 that are extended into the well when oil is detected may be used to determine the depth in the well of the air/oil interface. As the sensor unit 104 is additionally lowered into the well it may pass from being immersed in oil to being immersed in water. The lengths of the conductive paths 112, 114, 126, and/or 128 that are extended into the well when the sensor unit 105 indicates the change from oil to water may be used to determine the depth in the well of the oil/water interface.

In down-hole well applications, the microcontroller 106 may be contained in a controller unit 102 at the well head and may communicate with the sensor unit 104 in the well through one or more long cables. Instead of having multiple conductors, such as conductive paths 112, 114, 126, and 128 as shown in FIG. 1, a lower cost solution using a shielded single conductor cable 202 is illustrated in FIG. 4.

Figure 4:
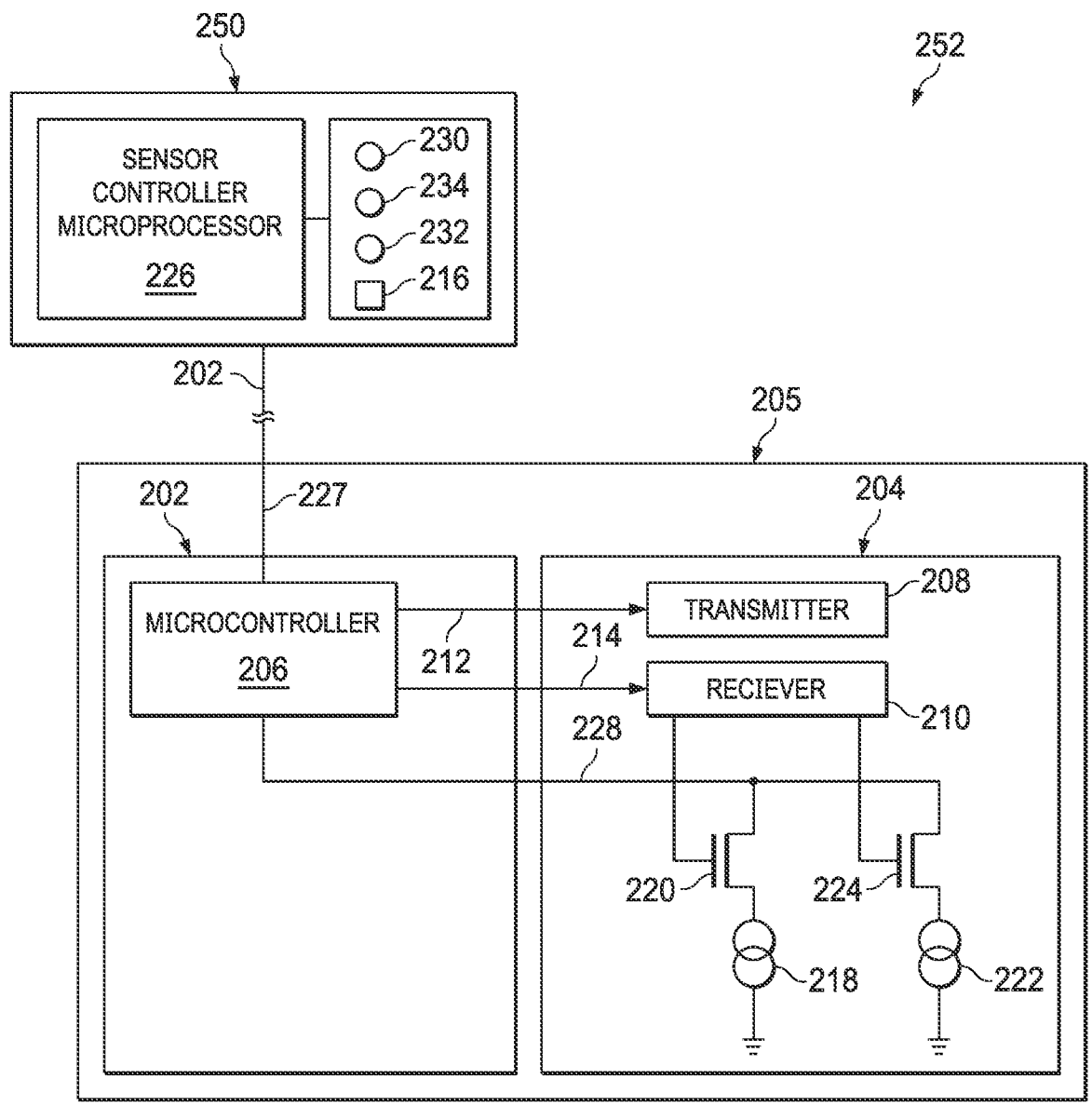
FIG. 4 depicts a sensor system in accordance with some embodiments.

FIG. 4 depicts a sensor system 252 that includes a sensor controller unit 250 and a sensor unit 205. The sensor controller unit 250 contains a sensor controller microprocessor 226 which is coupled to indicator lights which indicate if the sensor is located in air 232, oil 230, or water 234. A digital display 216 may also be included to indicate the status of other sensors such as temperature, pressure, conductivity, or the like. The sensor unit 205 may include a microcontroller 206, a transmitter 208, a receiver 210, transistor 220 and current source 218, and transistor 224 and current source 222. The transmitter 208 is connected to the microcontroller 206 by conductive path 212, and the receiver 210 is connected to the microcontroller 206 by conductive path 214. Sensor unit 205 is connected to sensor controller unit 250 by shielded single conductor cable 202. Receiver 110 is separately connected to each of transistors 220 and 224. Current sources 218 and 222 are connected in parallel to conductive path 228, which is connected to microcontroller 206. Microcontroller 206 is connected to shielded single conductor cable 202 by conductive path 227.

To determine fluid levels in an oil well, for example, the sensor unit 205 can be attached to the end of cable 202 and lowered down into the well. In some embodiments, the sensor system 252 may be set to repeatedly perform sequential detections to determine the medium in which the sensor unit 205 is immersed. For example, sensor unit 205 may be set to repeatedly perform sequential detections and then lowered into a well. In some cases, fluids at the top of a well may include air or natural gas. As such, the sensor unit 205, upon entering the well, may first send a current signal via cable 202 to controller unit 250 to indicate that it is immersed in air or natural gas (or in some embodiments controller unit 250 may determine that the sensor unit 205 is in air by not receiving a signal from sensor unit 205). When the sensor unit 205 passes from air into oil as it is being lowered into the well, the sensor unit 205 may then send a current signal to sensor controller unit 250 to indicate it is now immersed in oil. The length of the cable 202 that is extended into the well when oil is detected may be used to determine the depth in the well of the air/oil (or, e.g., gas/oil) interface. As the cable 202 length is additionally extended and the sensor unit 205 is additionally lowered into the well it may pass from being immersed in oil to being immersed in water. The length of the cable 202 that is extended into the well when the sensor unit 205 indicates the change from oil to water may be used to determine the depth in the well of the oil/water interface.

In some embodiments, the sensor controller unit 250 sends signals to the sensor unit 205 and receives signals from the sensor unit 205 through the mono-conductor cable 202.

In some embodiments it may be useful for the microprocessor 226 or microcontroller 206 to be able to distinguish between different current signals received from sensor 204. In some embodiments both the current source 218, which is used to indicate a detection of the RF signal transmitted at the transmit power for detecting oil, and the current source 222, which is used to indicate a detection of the RF signal transmitted at the transmit power for detecting water, are connected in parallel to the microcontroller 206 in the sensor unit 205. In one embodiment the current source 218 for detecting the RF signal transmitted at the transmit power for detecting oil may output a different current level than the current source 222 for detecting the RF signal transmitted at the transmit power for detecting water. In this arrangement, the microcontroller 206 can distinguish which RF transmit power signal was detected by the current level that is received. In another arrangement, the current source 218 may be identical to the current source 222. In this arrangement when the RF signal transmitted at the transmit power for detecting oil is detected only the current source 218 is turned on, whereas when the RF signal transmitted at the transmit power for detecting water is detected both the current source 218 and the current source 222 are turned on. In this arrangement, the microcontroller 206 detects a current level when the RF signal transmitted at the transmit power for detecting water is detected that is about double the current level when the RF signal transmitted at the transmit power for detecting oil is detected. When microcontroller 206 detects water it sends a current signal to the sensor controller microcontroller 226 that is about double the strength of the current signal it sends when it detects oil. The arrangement with identical current sources for oil 230 and water 234 is used for illustration only.

Figure 5:
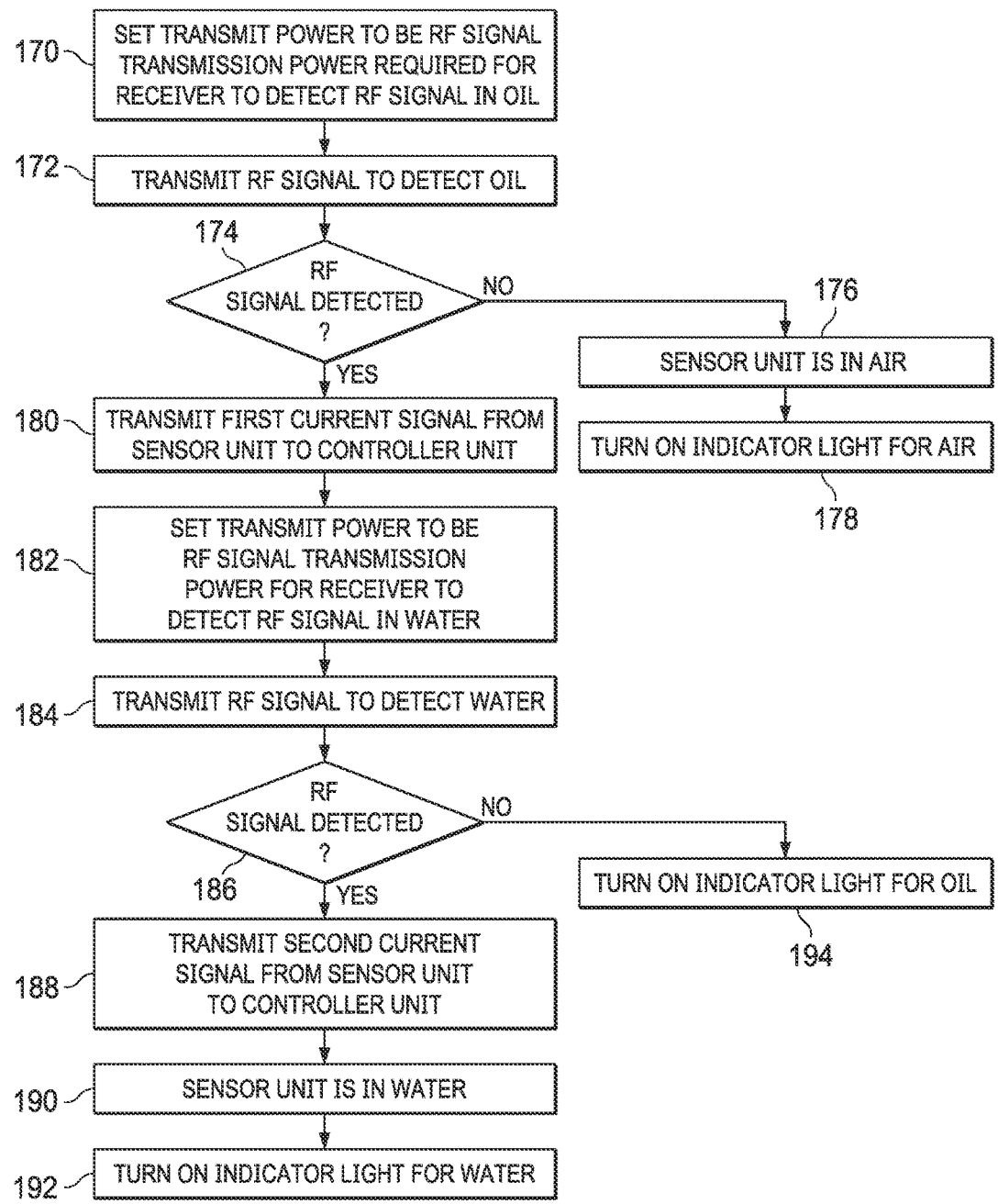
FIG. 5 depicts a method of operating a sensor system in accordance with some embodiments.

According to the discussion above, FIG. 5 depicts a method of using a sensor system (for example sensor system 252 depicted in FIG. 4) to determine the composition of a liquid or fluid. In some embodiments, the method may be initiated by a signal that is sent from microprocessor 226 to microcontroller 206 instructing the microcontroller 206 to initiate a detection process. In step 170, the transmit power of the RF signal that is transmitted from transmitter 208 is adjusted to be the RF transmit power for detecting oil. In some embodiments, microcontroller 206 may send a signal to the transmitter 208 on conductive path 212 to adjust the transmit power of the RF signal transmitted by the transmitter 208 to correspond to the transmit power of the RF signal for oil detection. The transmit power of the RF signal for oil detection may have been predetermined and or stored in a memory of the microcontroller 206 or sensor controller microprocessor 226, for example as using the methods as described in connection with FIG. 2. As such, the microcontroller 206 may retrieve the stored transmit power of the RF signal for oil detection from its own memory, or receive it from the sensor controller microprocessor 226, and send it to the transmitter 208 to instruct the transmitter 208 to transmit an RF signal using a transmit power that corresponds to the stored transmit power of the RF signal for oil detection. The microcontroller 206 also sends a signal on conductive path 214 to the receiver 210 indicating that the RF transmit power of the transmitter 208 is set at the RF transmit power for oil detection. In step 172, the transmitter 208 transmits the RF signal with the instructed transmit power for oil detection. In step 174, depending upon the fluid in which the sensor unit 205 is immersed, the receiver 210 either detects the RF signal, or does not detect the transmitted RF signal.

If the transmitted RF signal is not detected in step 174, in step 176 it is determined that the sensor unit 205 is in air. For example, the sensor controller microprocessor 226 may determine that the sensor unit 205 is in air after not receiving a current signal from the sensor unit 205 for a predetermined period of time after instructing the microcontroller 206 to begin a detection process or cause the transmitter 208 to transmit the RF signal. The sensor controller microprocessor 226 turns the air indicator light 232 on upon detecting that the sensor unit 205 is in air.

If the sensor unit 205 is in oil (or water, because water has a higher dielectric constant than oil), in step 174 the receiver 210 detects the RF signal. In step 180, logic in the receiver 210 turns on transistor 220 which connects a current source 218 to the sensor controller microcontroller 206 indicating that the sensor 204 has detected the transmitted RF signal. Microcontroller 206 may forward the current signal from current source 218 to microprocessor 226 using cable 202. In some embodiments, microcontroller 206 and/or microprocessor 226 may store a correspondence between a value of a received current signal and a fluid (or a transmit power level), enabling the microcontroller 206 and/or microprocessor 226 to identify which level of transmit signal was detected. Because a current signal from current source 218 is used to indicate to the sensor controller microprocessor 226 the detection of the transmitted RF signal, cable 202 may be relatively lengthy and the transmitted signal may still be reliably transmitted. For example, when a current signal is used, the signal may be less sensitive to degradation due to, for example, increased resistivity of cable 202 due for example to age or normal wear and tear.

Next, it may be determined whether the sensor unit 205 is in water. In step 182, the transmit power of the RF signal is adjusted to be the RF transmit power for detecting water. In some embodiments, the microprocessor 226 may send a signal to microcontroller 206, instructing the microcontroller to continue the detection process or instructing the microcontroller 206 to instruct the transmitter 208 to transmit an RF signal having a transmit power that corresponds to the RF transmit power for detecting water. The transmit power of the RF signal for water detection may have been predetermined and or stored in a memory of the sensor controller microprocessor 226, for example using the methods described in connection with FIG. 2. As such, the microcontroller 206 may receive the transmit power of the RF signal for water detection from the microprocessor 226 or may retrieve it from its own memory. In some embodiments, the microcontroller 206 may then send a signal to the transmitter 208 on conductive path 212 to decrease the transmit power of the RF signal to be the RF transmit power for detecting water. The microcontroller 206 also sends a signal to the receiver 210 indicating that the RF transmit power of the transmitter 208 is set at the transmit power for water detection. In step 184, the RF signal is transmitted by the transmitter 208 with the transmit power for detecting water. In step 186, the receiver 210 either detects the transmitted RF signal or does not detect the transmitted RF signal.

If the transmitted RF signal is not detected in step 186, in step 194 it is determined that the sensor unit 205 is in oil. For example, the sensor controller microprocessor 226 may determine that the sensor unit 205 is in oil after not receiving a current signal from the sensor unit 205 for a predetermined period of time after instructing the microcontroller 206 to instruct the transmitter 208 to transmit an RF signal having a transmit power that corresponds to the RF transmit power for detecting water. If the sensor controller microprocessor 226 determines the sensor unit 205 is in oil, it turns the oil indicator light 230 on.

If the transmitted RF signal is detected, in step 188 logic in the receiver 210 turns on transistor 224 which connects a current source 222 to the microcontroller 206 using conductive path 228, thereby sending a second current signal to the microcontroller 206 indicating that the transmitted RF signal has been detected. In some embodiments, a current that is provided by current source 218 has a magnitude that is different than a current that is provided by current source 222. As such, microcontroller 206 is able to distinguish between the first current signal and the second current signal. For example, microcontroller 206 may store an association between the first current signal and oil, and the second current signal and water. Microcontroller 206 may forward the second current signal from current source 222 to microprocessor 226 using cable 202.

In step 190, it is determined that the sensor unit 205 is in water. For example, the sensor controller microprocessor 226 may determine that the sensor unit 205 is in water after receiving the second current signal from the sensor unit 205. For example, microprocessor 226 may also store an association between the second current signal and water. In step 192, the water indicator light 234 is turned on.

Using constant current sources as a sensor signals instead of constant voltage levels may help to reduce or circumvent the problem of the sensor signal voltage level changing as the resistance of the cable 202 changes. The selected current signal, transmitted from the sensor unit 205 to the sensor controller unit 250 does not change when the resistance of the cable 202 between the sensor unit 205 and the sensor controller unit 250 changes. Accordingly, the same level of sensor current is transmitted regardless of changes in cable resistance. The cable resistance can change due to wear, age or due to a change in the cable length because of stretching or temperature variations.

Figure 6:
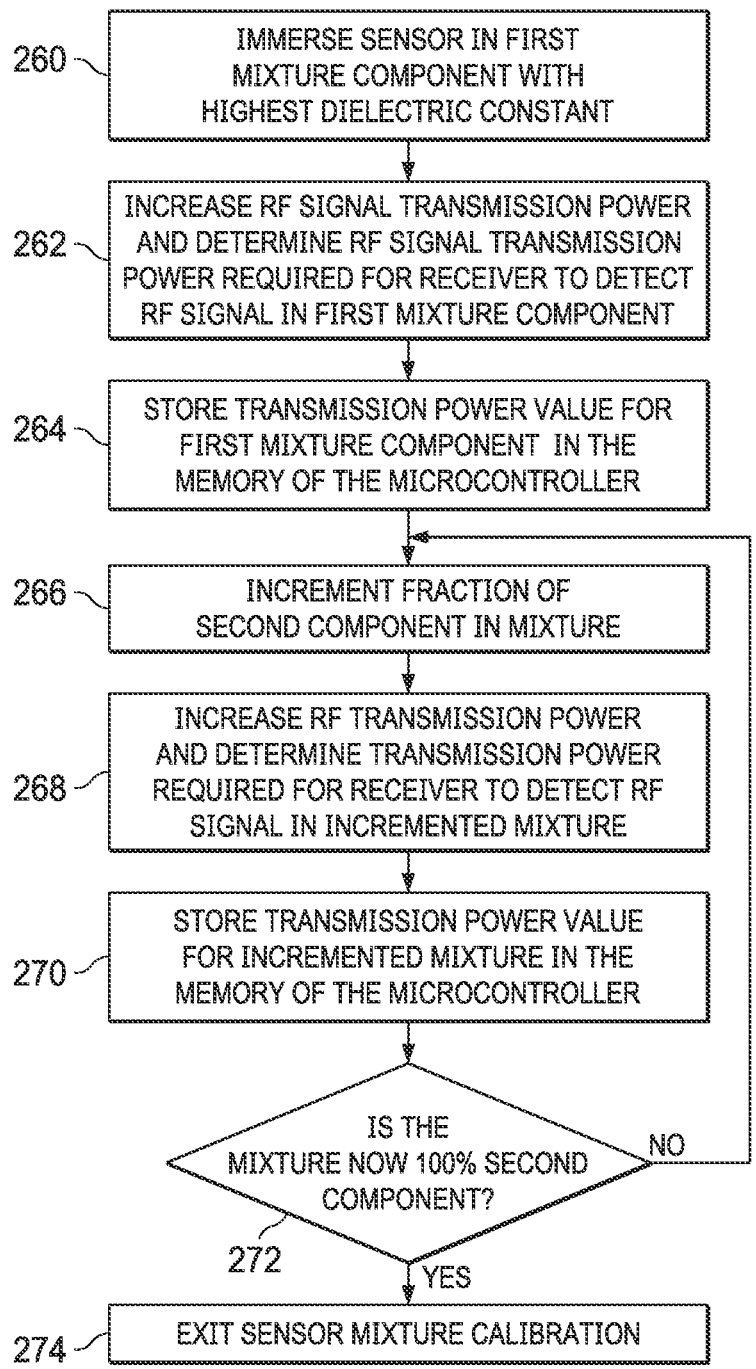
FIG. 6 depicts a method of calibrating a sensor system in accordance with some embodiments.

A method for calibrating a sensor system to determine the composition of a mixture of two fluids, such as sensor system 252 shown in FIG. 4, is described in the flow diagram in FIG. 6. This flow diagram describes a method for calibrating a fluid mixture where the dielectric constant of the mixture is reduced as the fraction of the second fluid in the fluid mixture is increased. The calibration can also be performed with a mixture whose dielectric constant is increased as the fraction of the second fluid is increased. The sensor system components referenced in connection with FIG. 6 are to sensor system 252 shown in FIG. 4.

FIG. 6 describes a method in which a dielectric constant of a fluid is incrementally reduced, and a transmit power that is required to be used to transmit an RF signal that can be detected is determined at each incremental step. In some embodiments, a same current source 218 or 222, or both, may be used to show the detection of a transmitted signal during the performing of the method shown in FIG. 6.

In step 260 of FIG. 6 the sensor unit 205 is first immersed in the first fluid mixture component only, where the first fluid mixture component has a higher dielectric constant than the second fluid mixture component. The fluid mixture component with the highest dielectric constant requires the lowest RF transmit power for the detector 110 to detect the RF signal. The first fluid may include a liquid, a gas, or a combination thereof. In some embodiments the first fluid includes air, oil, water, natural gas, or a mixture of two or more of these components.

In step 262 the RF transmit power is determined for detection of the first fluid mixture component. In some embodiments, the RF transmit power for detection of the first fluid is determined using the methods described above in connection with FIG. 2. For example, in some embodiments, the strength (for example, the transmit power) of the RF signal that is transmitted using transmitter 208 may initially be set to a low value, and then gradually increased until the receiver 210 first detects the RF signal. The transmit power of the RF signal that was used by transmitter 208 to transmit the RF signal when the receiver 210 first detected the RF signal may be determined to be the transmit power that is required to detect the RF signal in the first fluid mixture component. In some other embodiments, the transmit power of the RF signal transmitted by the transmitter may initially be set to a high value, and then gradually decreased until the receiver 210 is no longer able to detect the RF signal. The last transmit power used by the transmitter 208 to transmit the RF signal that resulted in a detected RF signal may be determined to be the transmit power that is required to detect the RF signal in the first fluid mixture component.

In step 264 this RF transmit power is stored in memory in the sensor controller microprocessor 226 as the transmit power that is required to detect the RF signal in the first fluid mixture component.

In step 266 a new mixture is created, where the fraction of the second component of the mixture with a lower dielectric constant is increased, thereby reducing the dielectric constant of the mixture being tested.

In step 268 the RF transmit power is increased and the RF transmit power for the receiver 210 to detect the second fluid is determined, for example using the same as, or similar methods as described in connection with step 262.

In step 270 the value for the RF transmit power for the receiver 210 to detect the RF signal in the incremented mixture is also stored in the memory of the sensor controller unit 250.

In step 272, it is determined whether the incremented mixture is now 100% the second fluid mixture component.

If, in step 272, it is determined that the incremented mixture is not 100% the second fluid mixture component, the method returns to step 266 and a new mixture is created with an incremented fraction of the second fluid mixture component. In some embodiments, each performing of step 266 may increment the fraction of the second fluid mixture component a same fractional amount in each iteration.

If, in step 272 it is determined that the incremented mixture is 100% the second fluid mixture component, the calibration method is complete.

Figure 7:
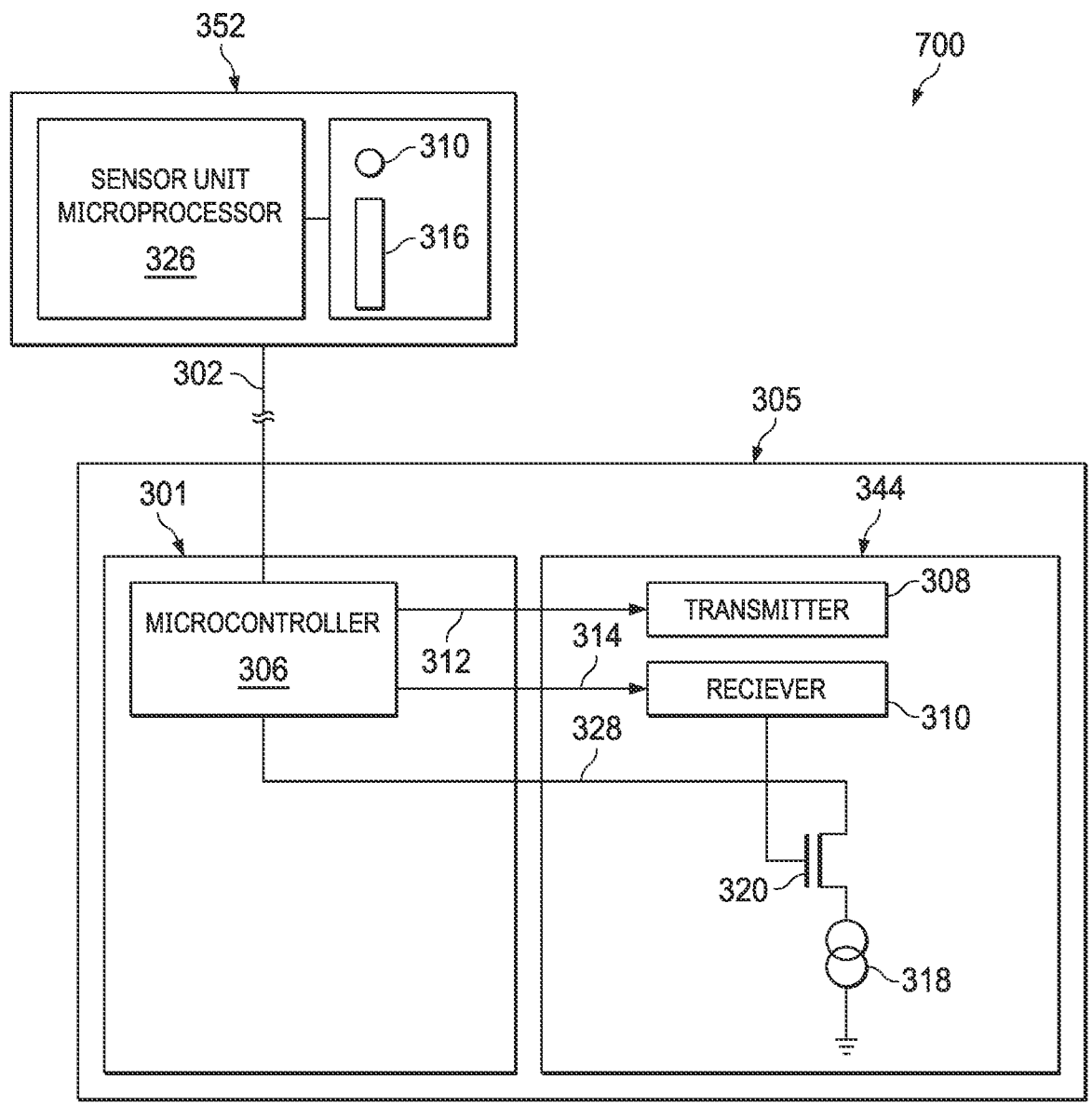
FIG. 7 depicts a sensor system in accordance with some embodiments.

A sensor system 700 for detecting a composition of a liquid mixture based upon a change in dielectric constant of the mixture is depicted in FIG. 7. Sensor system 700 includes a sensor controller unit 352 coupled to a sensor unit 305 by mono-conductor cable 302. In some embodiments, sensor controller unit 352 includes sensor unit microprocessor 326. Sensor controller unit 352 may also include a display, and the display may include one or more indicator lights 340 and digital display 316. Sensor unit 305 may include a controller unit 301 comprising microcontroller 306. Sensor unit 305 may also include sensor 344. Sensor 344 may include transmitter 308 and receiver 310. Transmitter 308 may be configured to transmit RF signals using various transmit powers. Transmitter 308 is connected to microcontroller 306 by conductive path 312. Receiver 310 may be configured to receive the transmitted RF signals. Receiver 310 is connected to microcontroller 306 by conductive path 314. Receiver 310 may also be connected to transistor 320, which may be connected to current source 318. Transistor 320 may be connected to microcontroller 306 by conductive path 328.

Figure 8:
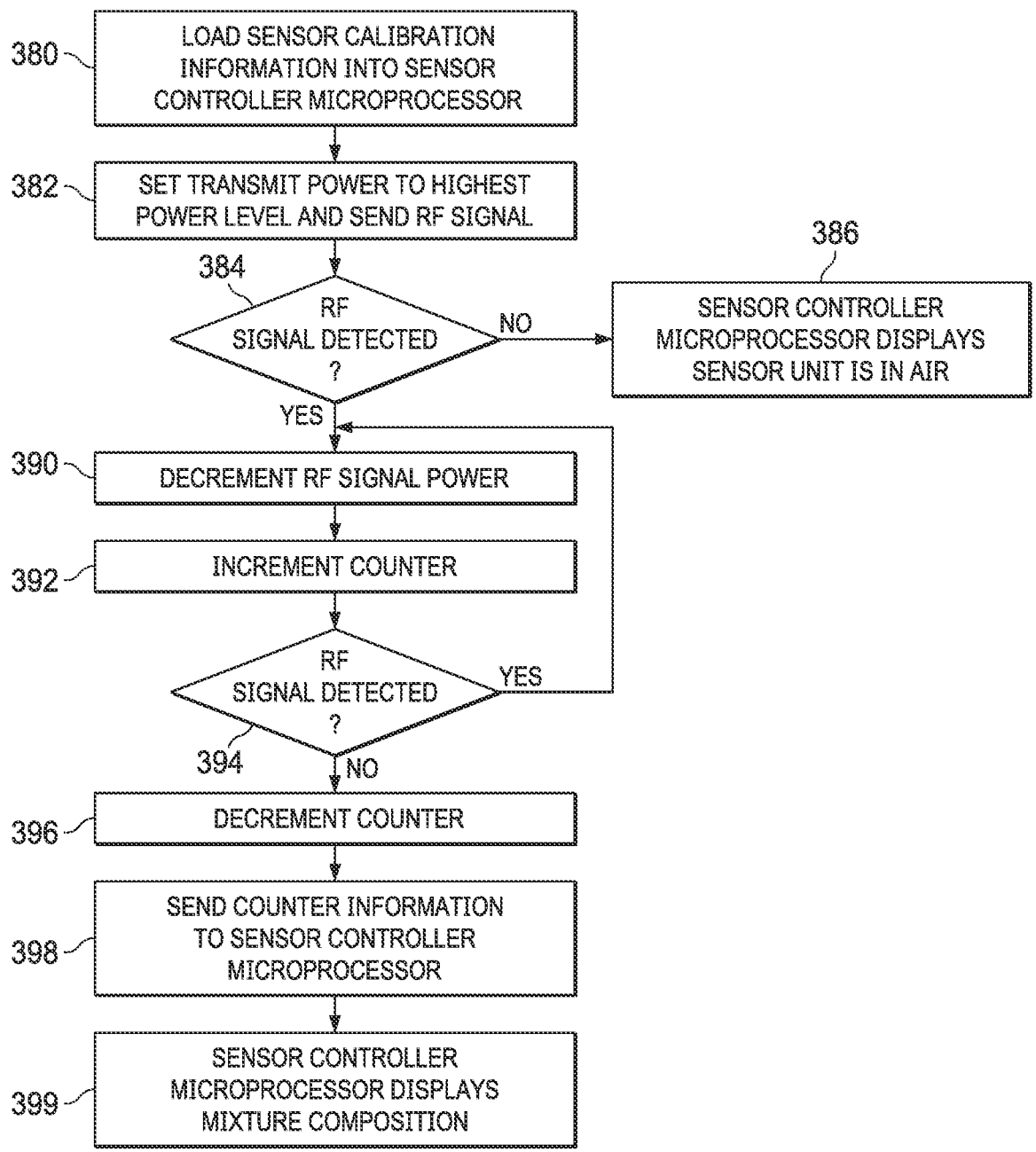
FIG. 8 depicts a method of operating a sensor system in accordance with some embodiments.

FIG. 8 depicts a method of using a sensor system (for example sensor system 700 depicted in FIG. 7) to determine the composition of a fluid mixture. In step 380 mixture calibration information is loaded into the memory of the sensor controller microprocessor 326. The mixture calibration information may have been predetermined, for example using the methods described in connection with FIG. 6. The mixture calibration information correlates a unique RF transmit power to each fluid mixture composition. The mixture calibration information may also correlate a unique RF transmit power with a counter value that is used by microcontroller 306.

In step 382, the transmit power of the RF signal that is transmitted from transmitter 308 is adjusted to be the highest RF transmit power for detecting a fluid mixture with the lowest dielectric constant. In some embodiments, sensor unit microprocessor 326 may send a signal to microcontroller 306 to begin a detection process, and timers in each of microcontroller 306 and microprocessor 326 may be initialized. In some embodiments, the signal that is sent from sensor unit microprocessor 326 to microcontroller 306 may include, or otherwise indicate, the highest RF transmit power for detecting a fluid mixture with the lowest dielectric constant. In some embodiments, microcontroller 306 may send a signal to the transmitter 308 on conductive path 312 to adjust the transmit power of the RF signal transmitted by the transmitter 308 to be the highest RF transmit power for detecting a fluid mixture with the lowest dielectric constant.

In step 384, if the RF signal with the highest transmit power is not detected, this means the sensor unit 305 is not in oil or water. Having not received a current signal from the sensor unit 305 for a predetermined amount of time after initialization of the timer in microprocessor 326, in step 386 the sensor controller microprocessor 326 indicates that the sensor unit 305 is in air on the display 316.

If the RF signal is detected in step 384, the RF transmit power is decremented in step 390 and the counter in microcontroller 306 is incremented.

If the RF signal with the reduced transmit power is detected in step 394, the transmit power is again decremented in step 390 and the counter again incremented in step 392.

Steps 394, 390, and 392 are repeated, with the RF signals being periodically sent, until the RF signal is no longer detected in step 394. When the RF signal is no longer detected in step 394 the counter is decremented in step 396 to the last counter value where the RF signal is detected.

In step 398 microcontroller 306 sends the counter information to the sensor controller microprocessor 326. Using the calibration information from step 380 the sensor controller microprocessor 326 determines the fluid mixture composition and indicates the mixture composition on the display 316.

In some embodiments, the method of FIG. 8 may be used to determine fluid levels in a well. For example, the sensor unit 305 is lowered down into the well. In some embodiments, the sensor system 700 may be set to repeatedly perform sequential detections (for example, using the method of FIG. 8) to determine the medium in which the sensor unit 305 is immersed. For example, the sensor unit 305 may be set to repeatedly perform sequential detections and then lowered into a well. In some cases, fluids at the top of a well may include air. As such, the sensor unit 305, upon entering the well, may first send no signal to the microprocessor 326, indicating that the sensor unit is in air (or in some embodiments may send a signal to the microprocessor 326 indicating air). When the sensor unit 305 passes from air into a first fluid (e.g., oil) as it is being lowered into the well, the sensor unit 305 may then send a current signal to microprocessor 326 to indicate it is now immersed in the first fluid. The length of the cable 302 that is extended into the well when the first fluid is detected may be used to determine the depth in the well of the air/first fluid interface.

As the sensor unit 305 is additionally lowered into the well it may pass from being immersed in the first fluid to being immersed in a second fluid, and the second fluid may be detected using the method of FIG. 8. The length of the cable 302 that is extended into the well when the sensor unit 305 indicates the change from the first fluid to the second fluid may be used to determine the depth in the well of the first fluid/second fluid interface.

Figure 9:
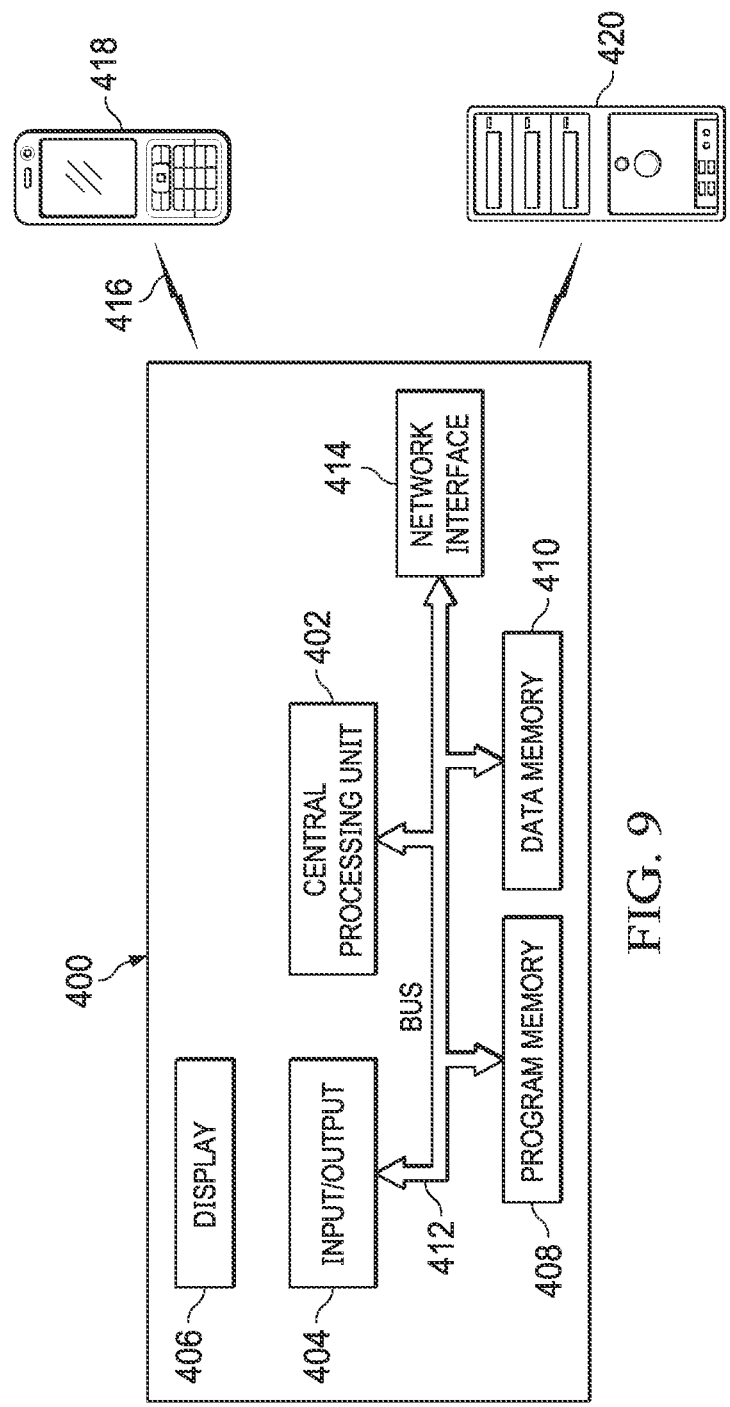
FIG. 9 depicts a block diagram of a processing system in accordance with some embodiments.

FIG. 9 is a block diagram of elements of a processing system 400 that may be used to implement a sensor microcontroller, for example sensor microcontroller 106 as described in connection with FIG. 1, sensor microcontroller 206 as described in connection with FIG. 4, and sensor microcontroller 306 and/or sensor microprocessor 326 as described in connection with FIG. 7. The processing system 400 may be equipped with one or more input/output devices 404, such as a video adapter/graphics processing unit ("GPU"). The processing system 400 may include a central processing unit ("CPU") 402/DSP, program memory 406, data memory 408, and a hardware accelerator connected to a bus 410.

The bus 410 may be one or more of any type of several bus architectures including a memory bus or memory controller, a peripheral bus, video bus, or the like. The CPU 402 may be formed with any type of electronic data processor. The memory, 406 and 408, may be formed with any type of system memory such as static random access memory (SRAM), dynamic random access memory (DRAM), synchronous DRAM (SDRAM), read-only memory (ROM), nonvolatile random access memory ("NVRAM"), a combination thereof, or the like. In an embodiment, the memory may include ROM for use at boot-up, and DRAM for data storage for use while executing programs. The program memory 408 may store programs, for example programs enabling the detection of an RF signal and an identification of a fluid or fluid mixture, for example as described in connection with FIGS. 1-8. For example, during calibration of a sensor system as described above, the determined RF transmit power required to receive an RF signal transmitted at the determined RF transmit power may be stored in the memory. The RF transmit power may later be retrieved and used to identify a composition of a fluid in which a sensor is immersed.

The video adapter/GPU 404 provides an interface to couple an external input and output from a display 406 to the processor 402. Display 406 may be the same as, or different to, display 216 as described in connection with FIG. 4 and/or display 316 as described in connection with FIG. 7. Other devices may be coupled to the processing system 400, and additional or fewer interface cards may be utilized. For example, a serial interface card (not shown) may be used to provide a serial interface for a printer.

The processing system 400 may also include a network interface 414, which can be a wired link, such as an Ethernet cable or the like, and/or a wireless link 416 to enable communication with a network such as a cellular communication network. The network interface allows the processor to communicate with remote units via the network. In an embodiment, the processing system 400 is coupled to a local-area network or a wide-area network to provide communications to remote devices, such as other processors 420, cell phones 418, the Internet, remote storage facilities, or the like.

It should be noted that processing system 400 may include other components. For example, processing system 400 may include power supplies, cables, a motherboard, removable storage media, cases, and the like. These other components, although not shown, are considered part of processing system 400.

While various embodiments of the present invention have been described above, it is understood that they have been presented by way of example only and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

What is claimed is:

1. A fluid sensor system, comprising:
   a fluid sensor, comprising:
      a radio frequency transmitter, configured to output radio frequency signals at adjustable levels of transmit power into a fluid;
      a radio frequency detector proximate to the radio frequency transmitter, configured to detect the radio frequency signals transmitted by the radio frequency transmitter into the fluid;
      a first constant current source; and
      a first switch coupled between the radio frequency detector and the first constant current source, wherein the fluid sensor including the radio frequency transmitter, the radio frequency detector, the first constant current source, and the first switch, is configured to be submerged as a whole into a fluid; and
   a microcontroller coupled to the radio frequency transmitter, coupled to the radio frequency detector, and coupled to the first constant current source.

2. The fluid sensor system of claim 1, wherein the fluid sensor comprises a plurality of constant current sources and a plurality of switches, wherein the first constant current source is comprised in the plurality of constant current sources, wherein the first switch is comprised in the plurality of switches, and wherein a switch of the plurality of switches is respectively coupled between each constant current source of the plurality of constant current sources and the radio frequency detector, and wherein each constant current source is coupled to the microcontroller; and
   wherein a memory stores a correspondence between each of the plurality of constant current sources and a material composition of a liquid.

3. The fluid sensor system of claim 1, wherein the microcontroller is configured to be located at a well head, and wherein the fluid sensor is configured to be located down hole and coupled to the microcontroller through a mono-conductor cable.

4. The fluid sensor system of claim 1, wherein a plurality of second constant current sources are each coupled to the radio frequency detector by a plurality of second switches;
   wherein the plurality of second constant current sources are each coupled to the microcontroller;
   wherein the microcontroller is at a well head; and
   wherein the radio frequency transmitter, the radio frequency detector, the first switch, the plurality of second switches, the first switch, and the plurality of second constant current sources are down hole and coupled to the microcontroller through a mono-conductor cable.

5. The fluid sensor system of claim 4, wherein the plurality of second constant current sources are electrically connected in parallel.

6. The fluid sensor system of claim 1, wherein the radio frequency transmitter is configured to output radio frequency signals at a first transmit power that is detectable by the radio frequency detector when the fluid sensor system is immersed in water and that is not detectable when the fluid sensor system is immersed in oil or is immersed in air.

7. The fluid sensor system of claim 1, wherein the fluid sensor system is configured in a manner that:
   when the fluid sensor is immersed in water and the radio frequency transmitter transmits a radio frequency signal using a transmit power that corresponds to a transmit power to be used to detect water, the radio frequency detector detects the radio frequency signal, the first switch is closed and the first constant current source sends a current signal to the microcontroller; and
   when the fluid sensor is immersed in air or oil and the radio frequency transmitter transmits a radio frequency signal using a transmit power that corresponds to a transmit power to be used to detect water, the radio frequency detector does not detect the radio frequency signal, the first switch is open, and the first constant current source does not send a current signal to the microcontroller.

* * * * *